United States Patent [19]
Williams

[11] Patent Number: 5,721,006
[45] Date of Patent: Feb. 24, 1998

[54] FINGERPRINTING SYSTEM

[76] Inventor: LeRoy A. Williams, 3006 Cravey Cove, Atlanta, Ga. 30345

[21] Appl. No.: 700,985

[22] Filed: Aug. 21, 1996

[51] Int. Cl.$^6$ .................................................. A61B 5/117
[52] U.S. Cl. ............................ 427/1; 427/341; 427/384; 118/31.5
[58] Field of Search ...................... 427/1, 341; 118/31.5

[56] References Cited

U.S. PATENT DOCUMENTS

| | | | |
|---|---|---|---|
| 3,851,619 | 12/1974 | Cofield, Jr. et al. | 118/31 |
| 4,262,623 | 4/1981 | Smith, III et al. | 118/31 |
| 4,379,178 | 4/1983 | Meadows et al. | 427/1 |
| 4,699,077 | 10/1987 | Meadows et al. | 118/31 |

*Primary Examiner*—Janyce Bell
*Attorney, Agent, or Firm*—Arnall Golden & Gregory, LLP.

[57] ABSTRACT

A fingerprinting system including a substrate treated with a reagent solution including an aromatic polyhydroxy compound and an antioxidant, and a developer solution including a color forming water soluble metal salt, wherein background "aging" of the substrate and coating is inhibited.

22 Claims, 2 Drawing Sheets

| SECURITY | |
|---|---|
| NAME | S. SECURITY NO. |
| ADDRESS | SEX |

FIG. 1

FINGERPRINTING SYSTEM

FIELD OF THE INVENTION

The present invention relates in general to an inkless fingerprint identification system and, more particularly, to a method for directly imaging fingerprints on a fingerprint card and inhibiting the fingerprint image from fading with time and the card from yellowing or darkening with age.

BACKGROUND OF THE INVENTION

There has long been a need for a simple system for permanently recording identifying images of the surface characteristics of various parts of the human body, such as the fingerprints, for identification purposes. The unusual patterns on the surface of the fingertips, for example, do not vary with time for an individual, and the pattern on each finger for any individual is unique. Thus, fingerprint comparison is an absolute means of identification. Because of the use of fingerprints in criminal proceedings as well as on identification cards for security systems, check identification means, and systems to be used in the future such as scanners, readers, and memory systems of computers and the like, the quality of recorded fingerprints must be high. In addition, an enduring image is preferred so that the identification means can be preserved for many years.

Recording fingerprints with the use of ink and paper is, of course, the simplest and perhaps oldest method. However, other methods have been developed, including ones which do not require the use of discoloring ink on the fingertips.

A patent to Heinecke, U.S. Pat. No. 2,082,735, discloses a method of obtaining a fingerprint wherein the finger is moistened with an oxidant solution, such as one containing ferric chloride and glycerin, and pressed on paper that has been coated with a reagent solution of gallic acid, thereby producing a dark, blue-black colored print due to the oxidation of gallic acid. Further patents in this area disclose the use of other oxidants such as ferric oleate, other ferric salts, vanadium salts, and other metal salts. Other reagents taught include tannic acid, propyl gallate, pyrogallol and phloroglucinol. Essentially, the use of aromatic polyhydroxy compounds are taught in U.S. Pat. No. 3,851,619 to Cofield, Jr. et al.

A patent issued to Meadows et al., U.S. Pat. No. 4,379,178, teaches the addition of a high molecular weight dibasic acid containing at least six carbon atoms, such as azelaic acid, to a reactant solution of either propyl gallate or a quinoline solution which is then coated on a paper card. A fingertip coated with an oxidizing solution is then applied to the card. This method purportedly gave a repeatedly distinct very dark fingerprint image and solved the problem of an aged coated card giving only a weak image.

The prior art methods of recording inkless fingerprints do not teach a method which will provide an enduring record of the fingerprint. The prior art methods provide a fingerprint image which may fade with time and wherein the coated or impregnated substrate on which the print is recorded upon will "yellow" or age with time. As the fingerprint image and the substrate ages, the fingerprint image may become less distinct and capable of identifying the individual. There is therefore a need for a method of fingerprinting which provides a more permanent record.

SUMMARY OF THE INVENTION

The present invention is drawn to methods for recording inkless fingerprints. The method utilizes a reagent solution for coating a background substrate in combination with a developer solution for coating the fingertip to be printed.

The fingertip is wetted with the developer solution and then applied to the substrate which has been coated with the reagent solution.

An innovative developer delivery apparatus that readily provides developer solution at a working concentration and amount to an applicator surface is also provided.

While the invention is disclosed as being useful for fingerprinting systems, it will be apparent to those of skill in the art that the method of inhibiting background oxidation is applicable to other processes.

BRIEF DESCRIPTION OF THE DRAWINGS

FIG. 1 is a top plan view of a fingerprint card prepared according to the present invention.

DETAILED DESCRIPTION

Figure 2:
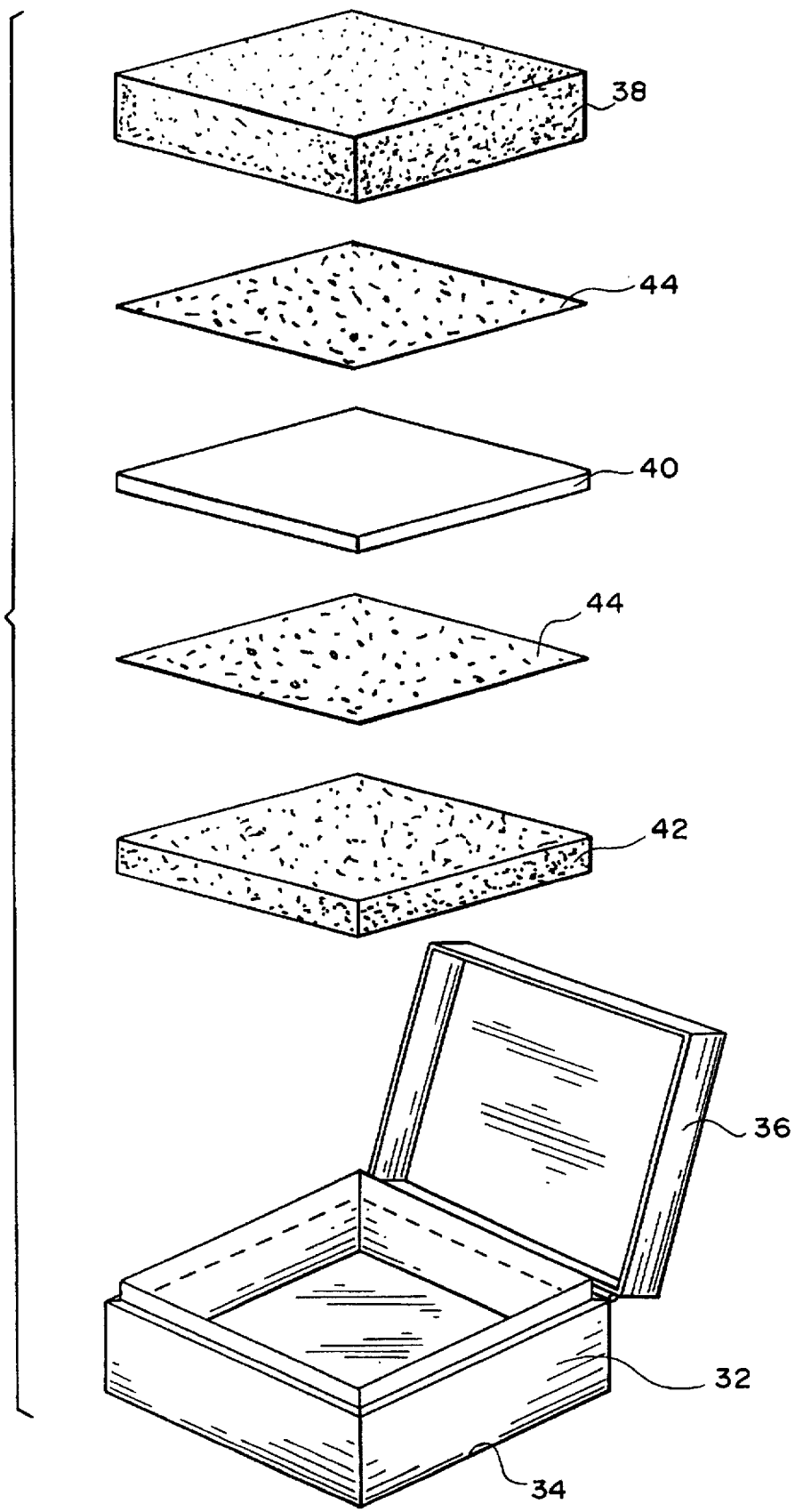
FIG. 2 is an exploded perspective view of the developer delivery apparatus of the present invention.

An improved fingerprinting identification system is provided in accordance with the present invention. The system produces a dark, distinct fingerprint image as an enduring record in a simple, efficient, and reliable manner and uses a technique and materials familiar to operators of fingerprinting systems. The fingerprint image produced according to the present invention develops rapidly and distinctly to form an identifying mark which is inhibited from fading within the useful life of the image. Furthermore, the substrate itself will not yellow or otherwise age with time within the useful life of the image. The typical useful life of a fingerprint image is generally from about 5 years to about 100 years.

Reagent Solution

Figure 1:
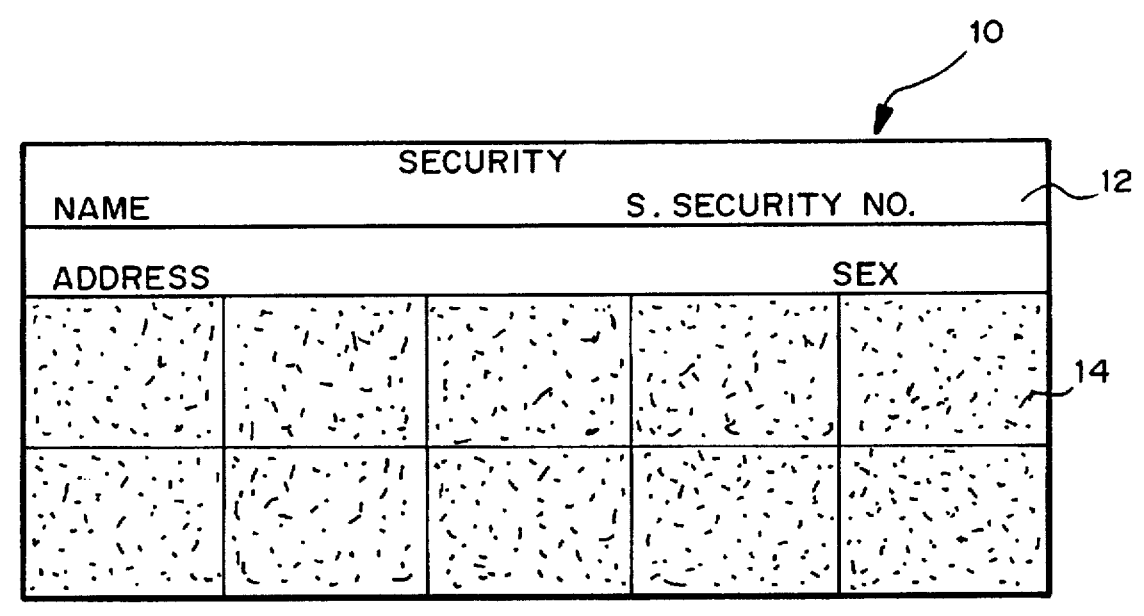

The fingerprinting system includes a reagent solution that is preferably applied to a substrate, such as absorbent fibrous material. Preferably, the substrate is a paper card and it can be a standard form designed by the Federal Bureau of Investigation of the United States and produced as the SIGNA-PRINT® card. This card, shown schematically in FIG. 1 and designated generally as numeral 10, preferably has an area 12 where identifying characteristics can be written, such as name, address, etc. The card also has an area designed to receive the fingerprint of each finger and designated spaces for the right four fingers together, etc. Fingerprint area 14 is coated with the reagent solution of the present invention, as described in more detail below. In general, any type of substrate can be used. However, the substrate should not be printed with water or alcohol based inks as these can be solubilized by the solutions of the present invention.

The reagent solution of the present invention includes a reagent chemical that is an aromatic polyhydroxy compound having the structural formula R—Ar(OH)$_n$, wherein R is a radical selected from the group consisting of hydrogen, halogens, amides, carboxyl groups, the n-propyl ester of monocarboxylic acids, and the like. Ar is an aromatic selected from the group consisting of benzene and naphthalene. N is a positive integer greater than 1, and, preferably, less than 4. Examples of reagents within the above definition include propyl gallate, gallic acid, tannic acid, pyrogallol, and phloroglucinol. An adequate amount of reagent chemical in the reagent solution is from about 2% by weight to about 20% by weight. The preferred reagent is about 6.5% by weight n-propyl gallate.

The reagent solution also preferably includes at least one thickening agent such as propylene glycol or some such agent which functions to thicken the solution so that it can be coated upon the substrate. The amount of thickener needed, thus, will depend upon the size and absorbency of the substrate to be coated. For a SIGNA-PRINT® card the amount of thickener needed ranges from about 4 to about 12% by volume. The preferred amount of propylene glycol is about 6% by volume.

At least one wetting agent is preferably added to facilitate coating of the solution onto the substrate. An example of an appropriate agent is TERGITOL®, a trade name for a 27% solution of sodium tetradecylsulfate, a surfactant/wetting agent sold by Union Carbide. Another wetting agent that can be used is TRITON® 770, a surfactant commonly sold as a 30% solution by Union Carbide. The surfactant/wetting agent is present in an amount ranging from about 0.015 to about 0.0006% by weight. In a preferred embodiment, the reagent solution includes about 0.00135% by weight TERGITOL® and 0.0015% by weight TRITON 770.

The reagent solution additionally preferably includes an optical brightener. Optical brighteners are commercially available and include LEUCOPHOR BMB and CARTAX DP liquid, optical brighteners made by Sandoz Chemicals Corporation. The optical brightener enhances the contrast between the background of the substrate and the print image. The optical brightner is present in an amount from about 0.0034% by weight to about 0.0041% by weight.

At least one antioxidant is added to the reagent solution, the antioxidant serving to control oxidation of the reagent. In particular, the addition of the antioxidant to the reagent solution that is coated onto the substrate card 10 eliminates "yellowing" or "aging" of the background substrate due to partial, slow oxidation of the coated reagent from minor oxidants such as atmospheric oxygen and sunlight. The antioxidant does not, however, prevent oxidation of the substrate coating by major oxidants such as ferric chloride. The antioxidant can be any that is soluble in the solution and is, most preferably, bisulfite and/or ascorbic acid.

The amount of antioxidant required depends upon the application for the reagent solution; i.e. what type of substrate it is to be applied to and the conditions under which the substrate will be used, i.e. merely stored in a dark file cabinet or used as an identification means frequently exposed to sunlight. The amount of antioxidant required, thus, is difficult to predict for every possible potential application but is anticipated to range from about 0.025% by weight to about 0.25% by weight. The preferred amount to be used on a SIGNA-PRINT® card, or the like, is about 37.5 g/L ascorbic acid and about 3.75 g/L sodium bisulfite. Other antioxidants can be used which are compatible with the other ingredients of the system and which do not function as "strong" antioxidants so as to inhibit oxidation of the reagent compound.

The reagent solution should also preferably include an ultra-violet (UV) protectant such as benzotriazole, which also prevents the reagent chemical from oxidizing. The amount of UV protectant needed will vary for the same reasons as the amount of antioxidant but should be present in an amount ranging from about 0.5 to 2.0% by weight. The preferred amount of benzotriazole for SIGNA-PRINT® cards is about 1.5% by weight. The solvent used for the solution is distilled water.

An example of a reagent solution made according to the present invention is set forth below.

| Reagent Solution - Example 1 | | |
|---|---|---|
| Ingredient | Function | Amount |
| propylene glycol | thickener | 60.0 cc |
| ascorbic acid | antioxidant | 37.5 g |
| sodium bisulfite | antioxidant | 3.75 g |
| CARTAX DP liquid 30% | optical brightener | 12.5 cc |
| benzotriazole | UV protectant | 15.0 g |
| TERGITOL ® 27% | surfactant/wetting agent | 5.0 cc |
| TRITON ® 770 30% | wetting agent | 5.0 cc |
| n-propyl gallate | reagent | 65 g |
| distilled water | solvent | up to 1000.0 cc total volume |

The above ingredients were mixed while slowly heating to approach 100° C. (avoid boiling) and then allowed to cool SIGNA-PRINT® cards were coated using a method which simulates the actions of a printing press. The reagent was applied to a roller which was rolled over the card using pressure. Only one application was needed to adequately coat the card. An important aspect of the coating method is that it applies an adequate amount of solution uniformly across the card areas to be used for print images.

Developer Solution

The improved developer solution of the present invention is formulated to have sufficient thickness so as to properly coat the fingertip or body member. For this purpose, a thickener such as propylene glycol is used. Preferably, propylene glycol is used in an amount from about 28.8% by volume to about 43.2% by volume, or most preferably, about 36.0% by volume.

A problem with prior developer solutions is that the solution was too "wet" on the fingertip and smudging of the fingerprint image resulted when the "wet" fingertip was pressed on the reagent coated substrate. To solve this problem, a certain amount of evaporative solvent was added to the present solution so that the drying rate of the solution is increased. The preferred solvent is isopropyl alcohol (IsOH) and it is preferably present at about 12% by volume, but can range from about 8% to about 15% by volume depending on the drying rate desired. Of course, other solvents can be used to advantage in the invention.

The developer chemical is a soluble metal salt reactive with the aromatic polyhydroxy reagent. The metal salt can be a metal from groups I to VIII of the periodic table and the anion may be a halide, sulfate, ferrocyanide, or the like. It is preferred that metal salts of iron and vanadium be used, and the preferred salt, due to its low cost and ready availability, is ferric chloride. Ferric chloride is commercially available as a 40% solution and it can be used in an amount of from about 300 to 700 ml per liter (12 to 28% by weight). Preferable, 500 ml per liter of a 40% by weight solution of ferric chloride is used.

A developer solution was prepared with the ingredients and amounts of Example 2.

| Developer Solution - Example 2 | |
|---|---|
| Ingredient | Amount |
| ferric chloride 40% | 500 cc |
| propylene glycol | 360 cc |
| IsOH | 120 cc |
| distilled water | up to 1000 cc total volume |

The developer solution prepared according to Example 2 is easily applied to a fingertip. The solvent will generally evaporate as the fingertip is applied to the substrate and the developer solution on the fingertip is of appropriate thickness so that the resulting print is rapidly formed and not smeared or smudged unless by inadvertent finger movement.

Developer Delivery Device

The developer delivery apparatus 30 is shown in FIG. 2 as comprising a container 32 having a base portion 34 and top portion 36 which fits tightly upon base portion 34 to provide a substantially air-tight container and prevent evaporation of the solvent when the apparatus is not in use. Top portion 36 can be hinged to base portion 34. Container 32 preferably is made of a plastic such as polypropylene and has a wall thickness of about 1/8 inch. The overall size is preferably about 4×6 inches or 3×5 inches with the base portion 34 being about 1/2–5/8 inches deep.

A sequence of pads arranged in a stack in the reservoir provides controlled delivery of the developer solution contained in container 32 to the top surface of the top pad. The pore sizes of the pads provide the desired amount of capillary action to deliver developer solution from the reservoir of the container to the top surface of the top pad.

The system of pads preferably includes a top pad 38 made of a hard porous material such as a ceramic pad or plate acquired from Coors Ceramic Company, Golden Colo. The pad has a pore size ranging from about 2 to 6 microns and is about 1/4 inch thick. Alternatively, a material purchased from OREC (Ozone Research and Equipment Company, Glendale, Ariz.) having a pore size of 3 microns with a range of 2 to 4 microns that is also ceramic can be used. The properties of this pad are that it is permeable to allow developer to pass through but does not hold excess solution on the top of the pad, i.e. the solution does not pool.

Two polypropylene metering pads underlay the ceramic pad 38. The first or top polypropylene pad 40 has a pore size of about 150–250 microns and a thickness of about 1/16 inch. The second or bottom polypropylene pad 42 has a pore size of about 250 microns to 500 microns and larger and a thickness of about 1/8 inch. The positioning of the larger pore size pad underneath the smaller pore size pad and the ceramic pad provides for controlled migration of developer through capillary action from the bottom of base portion 34 to the top surface of ceramic pad 38. The two plastic pads beneath the ceramic pad provide the "storage" capacity of the pad for extended service life. A plastic membrane sheet such as NOMEX™, a product manufactured by DuPont Corporation, non-woven sheet 44 can be placed between the two polypropylene pads and/or between the ceramic pad and top polypropylene pad if desired to obtain desired flow control. The non-woven sheets will act to slow the capillary movement of the solution and can be used to provide further control of the flow rate.

In use, the delivery apparatus 30 is assembled and developer solution is poured into the base portion 34 of the apparatus until the pads 40 and 42 are saturated. The apparatus 30 can be stored in this condition until ready for use, preferably with the lid 36 tightly closed. When it is desired to use the apparatus for making prints of an individual, the lid is opened and the individual places his or her fingertips on the top surface of ceramic pad 38 to coat the fingertips with developer. The fingertips are then pressed onto a reagent coated substrate. An image of the fingertips will appear.

While a preferred embodiment of the invention has been set out above, one skilled in the art may make modifications in the details of construction of the system and apparatus and the application of the method without departing from the spirit and scope of the invention as set out in the appended claims.

Wherefore, the following is claimed:

1. A fingerprint developing system, comprising:
   a reagent solution for coating a substrate comprising an aromatic polyhydroxy compound; and
   a developer solution comprising a color forming water soluble metal salt compound;
      wherein the reagent solution also includes an antioxidant which protects the coated substrate from oxidation by sunlight and atmospheric oxygen but does not prevent the coated substrate from oxidation by the color forming water soluble metal salt compound.

2. The fingerprint developing system of claim 1, wherein the reagent solution further comprises a thickener, a wetting agent, and an ultraviolet protectant.

3. The fingerprint developing system of claim 1, wherein the reagent solution further comprises an optical brightener.

4. The fingerprint developing system of claim 1, wherein said aromatic polyhydroxy compound has the structural formula R—Ar(OH)$_n$, wherein R is a radical selected from the group consisting of hydrogen, halogens, amides, carboxyl groups, and the n-propyl ester of monocarboxylic acids and Ar is an aromatic selected from the group consisting of benzene and napthalene, and n is a positive integer greater than 1 and less than 4.

5. The fingerprint developing system of claim 1, wherein the aromatic polyhydroxy compound is present in an amount ranging from about 2% by weight to about 20% by weight of the reagent solution.

6. The fingerprint developing system of claim 1, wherein the antioxidant is selected from the group consisting of ascorbic acid and its derivatives and bisulfites.

7. The fingerprint developing system of claim 1, wherein the antioxidant is a combination of ascorbic acid and sodium bisulfite.

8. The fingerprint developing system of claim 1, wherein the antioxidant is a combination of about 3.75 grams per liter ascorbic acid and about 0.375 grams per liter sodium bisulfite.

9. The fingerprint developing system of claim 1, wherein the reagent solution comprises about 6.5 percent by weight n-propyl gallate, about 3.75 grams per liter ascorbic acid, about 0.375 grams per liter sodium bisulfite, about 6 percent by volume propylene glycol, and about 0.00285 percent by weight wetting agent.

10. The fingerprint developing system of claim 1, wherein the developer solution comprises an iron or vanadium salt.

11. The fingerprint developing system of claim 1, wherein the developer solution comprises about 20 percent by weight ferric chloride, about 36 percent by volume propylene glycol, and about 12 percent by volume isopropyl alcohol.

12. The developing system of claim 1 wherein said developer solution is contained in a developer delivery apparatus comprising:
   a substantially air-tight container including a base portion and lid portion;
   a plurality of pads stacked in said base portion, each of said plurality having a different pore size range, said plurality of pads arranged in order of pore size so that the pad with largest pore size range is on the bottom of the stack; and
   a porous ceramic pad arranged on top of said plurality of pads.

13. The developer delivering apparatus of claim 12, wherein said plurality of stacked pads includes a first pad having a pore size of from about 150 microns to about 250 microns and a second pad having a pore size of from about 250 microns to about 500 microns and wherein the first and second pads are located beneath said porous ceramic pad which has a pore size of from about 2 microns to about 6 microns.

14. The developer delivering apparatus of claim 13, wherein said first pad has a thickness of about 1/16 inch, said second pad has a thickness of about 1/8 inch, and said ceramic pad has a thickness of about 1/4 inch.

15. A method of producing a print of a fingertip or other body part, comprising the steps of:

supplying a card coated with a reagent solution comprising an aromatic polyhydroxy compound;

applying a developer solution to the fingertip or other body part, said developer solution comprising a color forming water soluble metal salt compound; and applying the coated fingertip or other body part to said card so that an image forms on said card;

wherein the reagent solution also includes an antioxidant which protects the coated substrate from oxidation by sunlight and atmospheric oxygen but does not prevent the coated substrate from oxidation by the color forming water soluble metal salt compound.

16. The method of of claim 15, wherein the reagent solution further comprises a thickener, a wetting agent, and an ultraviolet protectant.

17. The method of of claim 15, wherein the reagent solution further comprises an optical brightener.

18. A method of inhibiting background oxidation of a substrate treated with a reagent solution including an aromatic polyhydroxy compound comprising including an antioxidant in said reagent solution which protects said treated substrate from oxidation by minor oxidants but does not prevent said treated substrate from oxidation by major oxidants, wherein the antioxidant is selected from the group consisting of ascorbic acid and its derivatives and bisulfites and combinations thereof.

19. The method of claim 18 wherein said antioxidant is ascorbic acid.

20. The method of claim 18 wherein said antioxidant is sodium bisulfite.

21. A fingerprint developing system, comprising:

a reagent solution for coating a substrate comprising an aromatic polyhydroxy compound and an antioxidant selected from the group consisting of ascorbic acid and its derivatives and bisulfites, and combinations thereof; and a developer solution comprising a color forming water soluble metal salt compound.

22. A method of inhibiting background oxidation of a substrate treated with a reagent solution including an aromatic polyhydroxy compound comprising including an antioxidant in said reagent solution which protects the coated substrate from oxidation by sunlight and atmospheric oxygen but does not prevent the coated substrate from oxidation by a water soluble metal salt compound.

* * * * *